United States Patent
Collins et al.

(10) Patent No.: US 6,579,686 B2
(45) Date of Patent: Jun. 17, 2003

(54) CONSTITUTIVE ANDROSTANE RECEPTOR

(75) Inventors: Jon L. Collins, Durham, NC (US); Derek J. Parks, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 36 days.

(21) Appl. No.: 09/814,569

(22) Filed: Mar. 22, 2001

(65) Prior Publication Data

US 2001/0055815 A1 Dec. 27, 2001

Related U.S. Application Data

(60) Provisional application No. 60/191,493, filed on Mar. 23, 2000.

(51) Int. Cl.$^7$ .............................................. G01N 33/53
(52) U.S. Cl. ........................................ 435/7.8; 435/7.5
(58) Field of Search .................................. 435/7.8, 7.5

(56) References Cited

FOREIGN PATENT DOCUMENTS

| WO | WO 99/50664 | 10/1999 |
|----|-------------|---------|
| WO | WO 99/60014 | 11/1999 |
| WO | WO 99/67637 | 12/1999 |

OTHER PUBLICATIONS

Voet et al. Biochemistry. 1990. John Wiley & Sons, Inc., pp. 126–128 and 228–234.*
Baes et al., "A New Orphan Member of the Nuclear Hormone Receptor Superfamily That Interacts with a Subset of Retinoic Acid Response Elements," *Molecular and Cellular Biology* 14:3 1544–1552 (Mar. 1994).
Beato et al.; "Steroid Hormone Receptors: Many Actors in Search of a Plot," *Cell* 83:851–857 (Dec. 1995).
Bertilsson et al., "Identification of a human nuclear receptor defines a new signaling pathway for CYP3A induction," *Proc. Natl. Acad. Sci. USA* 95:12208–12213 (Oct. 1998).
Blumberg et al., "SXR, a novel steroid and xenobiotic–sensing nuclear receptor," *Gene & Development* 12:3195–3205 (1998).
Choi et al., "Differential Transactivation by Two Isoforms of the Orphan Nuclear Hormone Receptor CAR," *The Journal of Biological Chemistry* 272:38 23565–23571 (Sep. 1997).
Forman et al., "Androstane metabolites bind to and deactivate the nuclear receptor CAR–β," *Nature* 395:612–615 (Oct. 1998).
Giguère et al., "Identification of a new class of steroid hormone receptors," *Nature* 331:91–94 (Jan. 1988).
Goodwin et al., "The Orphan Human Pregnane X Receptor Mediates the Transcriptional Activation of CYP3A4 by Rifampicin through a Distal Enhancer Module," *Molecular Pharmacology* 56:1329–1339 (1999).

Honkakoski et al., "The Nuclear Orphan Receptor CAR–Retinoid X Receptor Heterodimer Activates the Phenobarbital–Responsive Enhancer Module of the CYP2B Gene," *Molecular and Cellular Biology* 18:10 5652–5658 (Oct. 1998).
Jones et al., "The Pregnane X Receptor: A Promiscuous Xenobiotic Receptor That Has Diverged during Evolution," *Molecular Endocrinology* 14:1 27–39 (2000).
Kastner et al., "Nonsteriod Nuclear Receptors: What Are Genetic Studies Telling Us about their Role in Real Life?," *Cell* 83:859–869 (Dec. 1995).
Kawamoto et al., "Phenobarbital–Responsive Nuclear Translocation of the Receptor CAR in Induction of the CYP2B Gene," *Molecular and Cellular Biology* 19:9 6318–6322 (Sep. 1999).
Kliewer et al., "An Orphan Nuclear Receptor Activated by Pregnanes Defines a Novel Steroid Signaling Pathway," *Cell* 92:73–82 (Jan. 1998).
Kliewer et al., "Orphan Nuclear Receptors: Shifting Endocrinology into Reverse," *Science* 284:757–760 (Apr. 1999).
Kocarek et al., "Biphasic Regulation of Cytochrome P450 2B1/2 mRNA Expression by Dexamethasone in Primary Cultures of Adult Rat Hepatocytes Maintained on Matrigel," *Biochemical Pharmacology* 48:9 1815–1822 (1994).
Kocarek et al., "Comparative Analysis of Cytochrome P4503A Induction in Primary Cultures of Rat, Rabbit, and Human Hepatocytes," *Drug Metabolism and Disposition* 23:3 415–421 (1995).
Lehmann et al., "The Human Orphan Nuclear Receptor PXR is Activated by Compounds That Regulate CYP3A4 Gene Expression and Cause Drug Interactions," *J. Clin. Invest.* 102:5 1016–1023 (Sep. 1998).
Mangelsdorf et al., "The RXR Heterodimers and Orphan Receptors," *Cell* 83:841–850 (Dec. 1995).
Nichols et al., "Development of a Scintillation Proximity Assay for Peroxisome Proliferator–Activated Receptor γ Ligand Binding Domain," *Analytical Biochemistry* 257:112–119 (1998).
Parks et al., "Bile Acids: Natural Ligands for an Orphan Nuclear Receptor," *Science* 284:1365–1368 (May 1999).
Savas et al., "Molecular Mechanisms of Cytochrome P–450 Induction by Xenobiotics: An Expanded Role for Nuclear Hormone Receptors," *Molecular Pharmacology* 56:851–857 (1999).
Strom et al., "Use of Human Hepatocytes to Study P450 Gene Induction," *Methods In Enzymology* 272:388–401 (1996).

(List continued on next page.)

Primary Examiner—Yvonne Eyler
Assistant Examiner—Joseph F. Murphy
(74) *Attorney, Agent, or Firm*—Michael M. Conger

(57) ABSTRACT

The present invention relates, in general, to nuclear receptors and, in particular, to the Constitutive Androstane Receptor (CAR; NR 1I3) and to a method of identifying ligands therefor.

12 Claims, 4 Drawing Sheets

OTHER PUBLICATIONS

Sueyoshi et al., The Repressed Nuclear Receptor CAR Responds to Phenobarbital in Activating the Human CYP2B6 Gene,: *The Journal of Biological Chemistry* 274:10 6043–6046 (Mar. 1999).

Waxman, "P450 Induction by Structurally Diverse Xenochemicals: Central Role of Nuclear Receptors, CAR, PXR, and PPAR," *Archives of Biochemistry and Biophysics* 369:1 11–23 (Sep. 1999).

Moore et al., "Orphan nuclear receptors constitutive androstane receptor and pregnane X receptor share xenobiotic and steroid ligands," *The Journal of Biological Chemistry* 275(20):15122–15127 (May 2000).

Wei et al., "The nuclear receptor CAR mediates specific xenobiotic induction of drug metabolism," *Nature* 407:920–923 (Oct. 2000).

\* cited by examiner

CONSTITUTIVE ANDROSTANE RECEPTOR

CROSS REFERENCE TO RELATED CASES

This application claims the benefit of U.S. Provisional Application No. 60/191,493 filed Mar. 23, 2000.

BACKGROUND

1. Field of the Invention

The present invention relates, in general, to nuclear receptors and, in particular, to the Constitutive Androstane Receptor (CAR; NR 1I3) and to a method of identifying ligands therefor.

2. Background Information

Nuclear receptors are members of a superfamily of ligand-modulated transcription factors that mediate responses to a variety of agents including steroids, retinoids and thyroid hormones (see Beato et al, Cell 83:851 (1995); Kastner et al, Cell 83:859 (1995); Mangelsdorf et al, Cell 83:841 (1995)). Nuclear receptors have characteristic sequence motifs, for example, a variable amino terminal domain containing an autonomous activation function critical for cell and target specificity, a more carboxy terminal central region that contains a DNA binding domain and a distal carboxy terminal ligand binding domain (LBD). These motifs make it possible to isolate new nuclear receptor family members on the basis of sequence homology alone (Giguere et al, Nature 331:91 (1998)). Since isolation does not require prior identification of the receptor ligand, this technology has led to the discovery of multiple "orphan" receptors. Like receptors with known ligands, these orphan receptors contain sequence motifs characteristic of ligand binding domains. Thus, ligands may ultimately be found for these orphan receptors. Since nuclear receptors have importance as drug targets, the discovery of selective ligands for orphan receptors represents an important step towards finding novel pharmacological intervention pathways.

One member of the steroid/retinoid/thyroid hormone nuclear receptor superfamily of ligand-activated transcription factors, the CAR (originally named MB67), has been implicated in mediating the effects of xenobiotics on cytochromes P450 (CYPs) 2B and 3A (CYP2B and CYP3A, respectively) gene expression (Kliewer et al, Science 284 (5415):757–760 (1999), Savas et al, Mol. Pharmacol. 56:851–857 (1999), Waxman, Archives of Biochemistry & Biophysics 369(1):11–23 (1999)). CAR, a member of the nuclear receptor subfamily NR1, is most abundantly expressed in liver and has strong constitutive activity in cell-based reporter assays in the absence of any added ligand (Baes et al, Mol. Cell. Biol. 14:1544–1552 (1994), Choi et al, Journal of Biological Chemistry 272(38):23565–26571 (1997)). In HepG2 cells or other cell lines, exogenously expressed CAR can enter the nucleus and regulate the expression of reporter constructs. This constitutive activity can be inhibited by superphysiological concentrations of the testosterone metabolites androstanol and androstenol (Forman et al, Nature 395:612–615 (1998)). These androstanes inhibit the interaction of CAR with the coactivator protein SRC-1, suggesting that 'deactivation' is mediated by direct binding to the orphan receptor. In contrast to transfected cell lines, CAR is not present in the nucleus of primary hepatocytes but is instead sequestered in the cytoplasm. Treatment of primary hepatocytes with either phenobarbital (PB) or the planar hydrocarbon 1,4-bis[2-(3,5-dichloropyridyloxy)]benzene (TCPOBOP) results in the translocation of CAR into the nucleus, where it binds to its cognate DNA response elements as a heterodimer with the 9-cis retinoic acid receptor (RXR) and activates the transcription of target genes, including retinoic response elements (Baes et al, Mol. Cell. Biol. 14:1544–1552 (1994)) and CYP2B (Honkakoski et al, Mol. Cell. Biol. 18:5652–5658 (1998), Kawamoto et al, Molecular & Cellular Biology 19(9):6318–6322 (1999), Sueyoshi et al, Journal of Biological Chemistry 274(10):6043–6046 (1999)). CAR/RXR binding sites have been identified in the PB-responsive regions of the mouse, rat, and human CYP2B genes. The effects of PB on CYP2B expression are blocked by the phosphatase inhibitor okadaic acid (Kawamoto et al, Molecular & Cellular Biology 19(9):6318–6322 (1999)), suggesting that dephosphorylation of CAR, rather than direct ligand binding, is involved in its translocation into the nucleus.

The present invention provides a method of identifying CAR ligands. Such ligands can be used to elucidate the function of CAR, a potential drug discovery target, including its role in multicomponent regulatory networks. Additionally, this assay can be used to determine selectivity of ligands of other nuclear receptors, i.e., as a negative assay. Such an assay can be used to distinguish specific ligands for other nuclear receptors from non-specific ligands. Furthermore, this assay can be utilized as a secondary assay to a cell based CAR assay to verify that an effect seen in the cell based assay is directly on CAR. Additionally, this assay can be used to confirm that the effect of a compound in a fluorescence based cofactor assay is due to that compound binding at the binding pocket of CAR by virtue of its competitive displacement of clotrimazole.

SUMMARY OF THE INVENTION

The present invention relates to the nuclear receptor CAR and to a method of identifying ligands therefor. The method comprises assaying putative CAR ligands for their ability to displace clotrimazole from CAR LBD-containing proteins.

The present invention provides a method of screening a selected compound for its ability to inhibit the binding of clotrimazole to a Constitutive Androstane Receptor (CAR) ligand binding domain (LBD)-containing polypeptide comprising:

i) contacting said selected compound and clotrimazole with said CAR LBD-containing polypeptide under conditions such that clotrimazole can bind to said CAR LBD-containing polypeptide in the absence of said selected compound, and ii) determining the amount of clotrimazole bound to said CAR LBD-containing polypeptide and comparing that amount to an amount of clotrimazole bound to said CAR LBD-containing polypeptide in the absence of said selected compound, wherein a reduction in the amount of clotrimazole bound to said CAR LBD-containing polypeptide in the presence of said selected compound indicates that said selected compound inhibits the binding of clotrimazole to said CAR LBD-containing polypeptide.

The present invention further relates to a compound identifiable using the above method as being capable of inhibiting the binding of clotrimazole to CAR LBD. The instant invention further relates to a composition comprising such an identifiable compound.

The present invention additionally provides a method of determining whether a ligand for a selected nuclear receptor is non-specific for the selected nuclear receptor, comprising (a) contacting a ligand that binds the selected nuclear receptor with clotrimazole and a Constitutive Androstane Receptor (CAR) ligand binding domain (LBD)-containing polypeptide under conditions such that clotrimazole can bind to the CAR LBD-containing polypeptide in the absence of the ligand, and (b) determining the amount of clotrimazole bound to the CAR LBD-containing polypeptide, wherein an amount of clotrimazole bound to the CAR LBD-containing polypeptide that is less than that bound to the CAR LBD-containing polypeptide in the absence of ligand indicates that the ligand inhibits binding of clotrimazole to the CAR LBD-containing polypeptide and is non-specific in its binding to the selected nuclear receptor.

Further, the instant invention provides a method of screening a selected compound for ability to bind a human Constitutive Androstane Receptor (hCAR) ligand binding domain (LBD) comprising (a) contacting the selected compound and clotrimazole with the hCAR LBD-containing polypeptide under conditions such that clotrimazole can bind the hCAR LBD-containing polypeptide in the absence of the selected compound, and (b) determining the amount of clotrimazole bound to the hCAR LBD-containing polypeptide, wherein an amount of clotrimazole bound to the hCAR LBD-containing polypeptide that is less than that bound to the hCAR LBD-containing polypeptide in the absence of the selected compound indicates that the selected compound binds the hCAR LBD.

Objects and advantages of the invention will be clear from the description that follows.

BRIEF DESCRIPTION OF THE DRAWINGS

FIGS. 1A and 1B. Data represent the mean of assays performed in triplicate +/-S.E and are plotted as fold activation relative to transfected cells treated with vehicle alone. Cotransfection of mouse or human PXR (FIG. 1A) or hCAR or mCAR (FIG. 1B) expression plasmids with the CYP3A4-XREM-luciferase plasmid increased reporter levels 3.3-fold and 5.2-fold, respectively, relative to transfection with reporter plasmid alone. FIGS. 1C and 1D. Full dose response curves are shown for deactivators (FIG. 1C) or activators (FIG. 1D) of hCAR or mCAR.

FIG. 3A. Purified hCAR LBD was immobilized on scintillation proximity binding assay polyvinyltoluene beads and incubated with 10 nM [$^3$H]clotrimazole in the presence of increasing concentrations of unlabeled clotrimazole. No specific binding was observed in the absence of hCAR LBD (data not shown). FIG. 3B. Competition binding assays were performed with hCAR LBD and 10 nM [$^3$H]clotrimazole and 10 $\mu$M of each of the competitors, except phenobarbital, which was tested at 1 mM. Data represent the mean of assays performed in duplicate +/-S.E.

DETAILED DESCRIPTION OF THE INVENTION

Figure 1A:
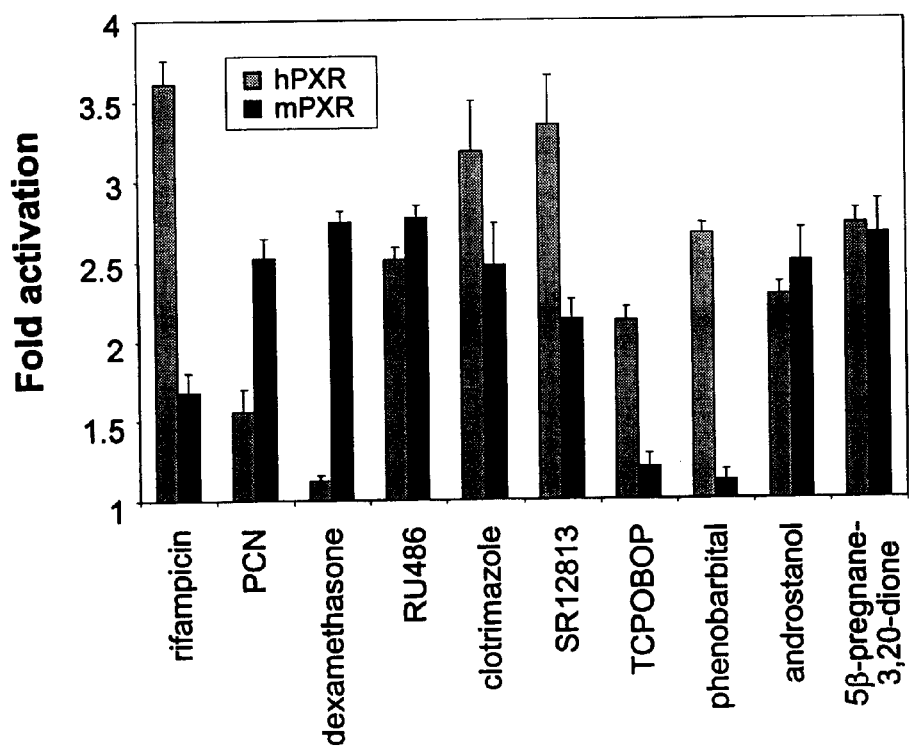
FIGS. 1A to 1D. Effects of xenobiotics on CAR and PXR activity. CV-1 cells were transfected with expression plasmids for mouse PXR (mPXR) or human PXR (hPXR) (FIG. 1A), or for mouse CAR (mCAR) or human CAR (hCAR) (FIG. 1B), and the XREM-CYP3A4-luciferase reporter. Cells were treated with 10 $\mu$M of each compound, except for phenobarbital, which was tested at 0.5 mM. Cell extracts were subsequently assayed for luciferase activity.

The present invention relates to the orphan nuclear receptor, CAR, and to methods of identifying ligands for this receptor. The present invention is based, at least in part, on the discovery that the anti-fungal agent, clotrimazole, is a potent inhibitor of the hCAR/SRC-1 interaction (IC$_{50}$~100 nM).

The method of the present invention takes the form of a competition binding assay. In accordance with this method, a polypeptide or protein comprising CAR LBD (e.g., human CAR LBD (hCAR LBD)) (e.g., hCAR, a portion (fragment) of hCAR including hCAR LBD, hCAR LBD or a fusion protein comprising hCAR LBD) is contacted, in a reaction mixture, with clotrimazole, advantageously bearing a detectable label (e.g., a radioactive or fluorescent label). As used in this assay, CAR LBD can comprise that portion of CAR LBD sufficient for binding of a ligand. A selected compound (putative ligand) (proteinaceous or non-proteinaceous) is added to the reaction mixture and assayed for its ability to compete with the clotrimazole (e.g., labeled) for binding to the CAR LBD-containing polypeptide. Free clotrimazole can be separated from bound clotrimazole, and the amount of bound (or free) clotrimazole determined to assess the ability of the selected compound (putative ligand) to compete. This assay can be formatted so as to facilitate screening of large numbers of test compounds, for example, by linking the CAR LBD-containing polypeptide to a solid support so that it can be readily washed free of unbound reactants.

Thus, the present invention provides a method of screening a selected compound for its ability to inhibit the binding of clotrimazole to a Constitutive Androstane Receptor (CAR) ligand binding domain (LBD)-containing polypeptide comprising:

i) contacting said selected compound and clotrimazole with said CAR LBD-containing polypeptide under conditions such that clotrimazole can bind to said CAR LBD-containing polypeptide in the absence of said selected compound, and ii) determining the amount of clotrimazole bound to said CAR LBD-containing polypeptide and comparing that amount to an amount of clotrimazole bound to said CAR LBD-containing polypeptide in the absence of said selected compound, wherein a reduction in the amount of clotrimazole bound to said CAR LBD-containing polypeptide in the presence of said selected compound indicates that said selected compound inhibits the binding of clotrimazole to said CAR LBD-containing polypeptide.

The present invention further provides a method of determining whether a ligand for a selected nuclear receptor is non-specific for the selected nuclear receptor, comprising i) contacting a ligand that binds the selected nuclear receptor with clotrimazole and a human Constitutive Androstane Receptor (hCAR) ligand binding domain (LBD)-containing polypeptide under conditions such that clotrimazole can bind to the hCAR LBD-containing polypeptide in the absence of the ligand, and ii) determining the amount of clotrimazole bound to the hCAR LBD-containing polypeptide, wherein an amount of clotrimazole bound to the hCAR LBD-containing polypeptide that is less than that bound to the hCAR LBD-containing polypeptide in the absence of ligand indicates that the ligand inhibits binding of clotrimazole to the hCAR LBD-containing polypeptide and is non-specific in its binding to the selected nuclear receptor.

The present invention additionally provides a method of screening a selected compound for ability to bind a human Constitutive Androstane Receptor (hCAR) ligand binding domain (LBD) comprising i) contacting the selected compound and clotrimazole with the hCAR LBD-containing polypeptide under conditions such that clotrimazole can bind the hCAR LBD-containing polypeptide in the absence of the selected compound, and ii) determining the amount of clotrimazole bound to the hCAR LBD-containing polypeptide, wherein an amount of clotrimazole bound to the hCAR LBD-containing polypeptide that is less than that bound to the hCAR LBD-containing polypeptide in the absence of the selected compound indicates that the selected compound binds the hCAR LBD.

CAR-LBD-containing proteins suitable for use in the assays described above can be prepared by any desired method as is known to those of skill in the art, for example, recombinantly (see Examples that follow). As regards CAR LBD-containing fusion proteins, preferred are fusion proteins that include an identifiable or capturable tag, such as a His tag (see Examples). The non-CAR LBD-containing moiety of the fusion protein can be located N-terminal or C-terminal to the CAR LBD-containing moiety. A CAR LBD-containing protein or polypeptide can be of any desirable length, including oligopeptides, polypeptides and full length proteins. The word "polypeptide" is typically used in the claims to include any length polypeptide. A human CAR LBD-containing polypeptide can have a human CAR LBD and can have additional sequences (CAR or non-CAR) from human or from a non-human species. For example, a reporter construct comprising a CAR LBD and a reporter coding sequence can be utilized.

As indicated above, the CAR LBD-containing polypeptide can be present linked to a solid support, including a plastic or glass plate or bead, a chromatographic resin, a filter or a membrane. Methods of attachment of proteins to such supports are well known in the art and include direct chemical attachment and attachment via a binding pair (e.g., biotin and avidin or biotin and streptavidin). It will also be appreciated that, whether free or bound to a solid support, the CAR LBD-containing polypeptide can be unlabeled or can bear a detectable label (e.g., a fluorescent or radioactive label).

Conditions such that clotrimazole can bind the CAR or hCAR LBD-containing polypeptide in the absence of the selected compound or ligand can be readily determined by means that will be apparent to the skilled artisan in light of the present invention and the Examples herein, and such conditions are exemplified in the Examples.

In a preferred embodiment, the present invention relates to a high-throughput scintillation proximity binding assay for CAR (see Example 3). In accordance with this approach, a selected compound (putative CAR ligand) can be added to a reaction mixture comprising radiolabled clotrimazole (e.g., $^3$H-clotrinazole) and beads (e.g., polyvinyltoluene SPA beads) coated with CAR LBD-containing polypeptide. The reaction mixture can be present, for example, in a well of a 96 well SPA plate. The plate can be incubated under conditions such that binding of clotrimazole to the CAR LBD-containing polypeptide in the absence of the selected compound can occur (which can be readily assessed and e.g., can be for about 1 hour at room temperature). The amount of bound radioactivity for each well can be determined, for example, in a Wallac 1450 Microbeta counter. The amount of bound radioactivity observed in the presence of the selected compound can be compared with the amount of bound radioactivity observed in the absence of the selected compound to determine the affinity of the selected compound for CAR LBD.

A compound that is non-specific in its binding to a receptor is one that can bind a receptor other than the receptor to which it is known to bind. Typically, relevant non-specific binding is binding that occurs under physiological conditions.

The invention also relates to compounds identifiable as CAR or hCAR ligands using the above-described method, to compositions comprising such compounds and to methods of using same. Such compositions can contain a carrier; such carrier can be, for example, a pharmaceutically acceptable carrier, such as an excipient, a diluent, an adjuvant. By "pharmaceutically acceptable" is meant that the material is not biologically or otherwise undesirable and does not interact in a deleterious manner with any other component of the composition of which it is a component. Compounds identified using the assay of the present invention as being capable of binding CAR LBD can be used to elucidate the function of CAR, including its role in multicomponent regulatory networks.

The data presented in the Examples that follow establish CAR as a bona fide receptor and show that the progesterone metabolite 5β-pregnane-3,20-dione binds to CAR and activates the receptor above its high basal level of activity. The androstanes were previously shown to deactivate CAR in cell-based assays, lowering its transcriptional activity below the basal level (Forman et al, Nature 395:612 (1998)). Although superphysiological concentrations of 5β-pregnane-3,20-dione and androstanol are required for these effects, the data indicate that physiological steroidal ligands exist that can either activate and deactivate CAR. CAR regulates the expression of CYPs, which are involved in the oxidative metabolism of natural steroid hormones as well as xenobiotics. CAR may be one component of a regulatory network that governs endocrine hormone homeostasis. The availability of robust cell-based assays for CAR and high throughput binding assays, provided by the present invention, make possible the search for the natural ligands for this orphan receptor. Ligands of CAR, natural or non-natural, can themselves have numerous uses, such as regulation of oxidative metabolism and/or regulation of endocrine hormone homeostasis.

Certain aspects of the present invention are described in greater detail in the Examples that follow.

EXAMPLES

The experimental details that follow are relevant to the specific Examples that below.

Cotransfection assays. CV-1 cells (a monkey kidney epithelial cell line) were plated in 96-well plates at a density of 20,000 cells/well in DME high glucose medium supplemented with 10% charcoal/dextran treated fetal bovine serum (Hyclone, Logan, Utah). Transfection mixes contained 5 ng of receptor expression vector, 20 ng of reporter plasmid, 12 ng of β-actin secreted placental alkaline phosphatase (SPAP) as internal control, and 43 ng of carrier plasmid (control). The XREM-CYP3A4-LUC reporter was as previously described (Goodwin et al, Mol. Pharmacol. 56(6):1329–1339 (1999)). Human and mouse PXR expression plasmids were as described previously (Kliewer, S. A. et al. Cell 92:73–82 (1998); Lehmann, J. M. et al. J. Clin. Invest. 102:1016–1023 (1998)). Transfections were performed with LipofectAMINE (Life Technologies, Rockville, Md.) essentially according to the manufacturer's instructions. Drug dilutions were prepared in phenol red-free D-MEM/F-12 with 15 mM HEPES supplemented with 10% charcoal stripped, delipidated calf serum (Sigma Chemical Co., St. Louis, Mo.). Cells were incubated for 24 hours in the presence of drugs, then the medium was sampled and assayed for alkaline phosphatase activity. Luciferase reporter activity was measured using the LucLite assay system (Packard Instrument Company, Meriden, Conn.).

Overexpression, purification and biotinylation of hCAR and PXR LBDs. The mCAR and hCAR LBD were each expressed in E. coli strain BL21(DE3) as a polyhistidine-tagged fusion protein. Sequence encoding a modified polyhistidine tag (MKKGHHHHHHG (SEQ ID NO.:2)) was fused in frame to sequence encoding residues 113–358 of mCAR (Choi, H. S. et al. J. Biol. Chem. 272:23565–23571 (1997) or 103–348 of hCAR (Baes, M. et al. Mol. Cell. Biol. 14:1544–1552 (1994) and subcloned into the pRSETa expression vector (Invitrogen). The resulting complete encoded sequence is set forth as SEQ ID NO.:1. Cells were grown at 25° C. in LB medium with 0.1 mg/mL carbenicillin for approximately 20 hours before harvesting. Routinely, 60–70 g of cell paste was resuspended in 400–450 ml TBS (25 mM Tris, pH 8.0, 150 mM NaCl). Cells were lysed by passing 3 times through an APV Rannie MINI-lab homogenizer and cell debris was removed by centrifugation (30 minutes, 20,000 g, 4° C.). After adjusting the imidazole concentration to 50 mM, the lysate was loaded onto a column packed with Sepharose [$Ni^{++}$ charged] Chelation resin (Pharmacia) and pre-equilibrated with TBS pH 8.0/50 mM imidazole. After washing to baseline absorbance, the column was washed with approximately one column volume of TBS pH –8.0 containing 72.5 mM imidazole. The recombinant protein was eluted with a gradient from 50 to 500 mM imidazole. Column peak fractions were pooled immediately and diluted 5–7 fold with 25 mM Tris pH 8.0, containing 5% 1,2-propanediol, 0.5 mM EDTA and 5 mM DTT. The diluted protein sample was then loaded onto a column packed with Poros HQ resin (PerSeptive Biosystems) and eluted with a gradient from 0–500 mM NaCl. Peak fractions were pooled and concentrated using Centri-prep 10K (Amicon) and subjected to size exclusion, using a column packed with Superdex-75 resin (Pharmacia) pre-equilibrated with TBS, pH 8.0, containing 5% 1,2-propanediol, 0.5 mM EDTA and 5 mM DTT.

The purified CAR LBDs were desalted/buffer exchanged using PD-10 gel filtration columns into PBS [100 mM NaPhosphate, pH 7.2, 150 mM NaCl]. CAR LBDs were diluted to approximately 10 mM in PBS and five-fold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000×molar excess of Tris-HCl, pH 8. The modified CARa LBDs were dialyzed against 4 buffer changes, each of at least 50 volumes, PBS containing 5 mM DTT, 2 mM EDTA and 2% sucrose. The biotinylated CAR LBDs were subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to three. HPXR was coexpressed with an 88-amino acid fragment of SRC-1 and purified to homogeneity for use in radioligand binding assays as described previously (Jones, et al.)

Fluorescence resonance energy transfer (FRET) ligand sensing assay. The FRET ligand sensing assay was performed by modification of a previously published procedure (Parks et al, Science 284:1365–1368 (1999)). Biotinylated mCAR and hCAR LBD was labeled with the streptavidin-conjugated fluorophore allophycocyanin. Labeled CAR LBDs were incubated with a peptide that included the second LXXLL (SEQ ID NO.:3) motif of human SRC-1 (amino acids 676 to 700) labeled with europium chelate. Data were collected with a Wallac Victor fluorescence reader in a time resolved mode as previously described (Parks et al, Science 284:1365–1368 (1999)) and the fluorescence ratio calculated.

Scintillation proximity binding assay. Streptavidin polyvinyltoluene SPA beads (Amersham Pharmacia Biotech) were resuspended in assay buffer (50 mM Tris, 50 mM KCl, 1 mM CHAPS, 0.1 mg/ml BSA, 10 mM DTT). Biotinylated hCAR LBD was added to a final concentration of 50 nM. The amount of biotinylated receptor can be varied to account for variations in the extent of biotinylation and/or the observed S/N ratio for different batches of receptor. In general the receptor concentration was increased above 100 nM only for those preparations that had a low extent of receptor biotinylation. The receptor/bead mixture was allowed to incubate at room temperature for 15 min with gentle agitation. Uncoupled receptor was removed by centrifuging the receptor/bead mixture at 2500 rpm for 10 min and pouring off the supernatant. Receptor-coupled beads were resuspended in assay buffer and a second wash performed. All experiments were run in Costar 96-well SPA plates using an assay volume of 100 $\mu$l. Typically, reactions included receptor-coated beads, 10 nM [imidazole $^3$H]clotrimazole and the indicated concentrations of competitor compounds. SPA plates were incubated for 1 hour at room temperature and counted in a Wallac 1450 Microbeta counter. (See Nichols et al, Anal. Biochem. 257(2):112–119 (1998).) PXR scintillation proximity binding assays were performed as described previously (Jones, S. A. et al. Mol. Endocrinol. 14:27–39(2000)).

Example 1

Activity of Xenobiotics and Steroids on CAR

The mouse and human CAR and PXR were tested in transfection assays in CV-1 cells with xenobiotics that are well-established inducers of CYP2B and/or CYP3A gene expression. The xenobiotics evaluated included PB, TCPOBOP, the macrolide antibiotic rifampicin, the synthetic pregnane pregnenolone 16α-carbonitrile (PCN), the synthetic glucocorticoid dexamethasone, the antiprogestin RU486, the antimycotic clotrimazole, and the cholesterol-lowering drug SR12813. The sex steroid metabolites 5β-pregnane-3,20-dione and 5α17α-androstanol, which deactivate CAR and activate PXR, were also included As a reporter, the recently described XREM-CYP3A4-LUC construct was used which contains the enhancer region (nucleotides −7836 to −7208) and promoter (nucleotides −362 to +53) of CYP3A4 driving luciferase gene expression (Goodwin et al, Molecular Pharmacology 56(6):1329–1339 (1999)). This reporter construct is highly responsive to both CAR and PXR.

Figure 1B:
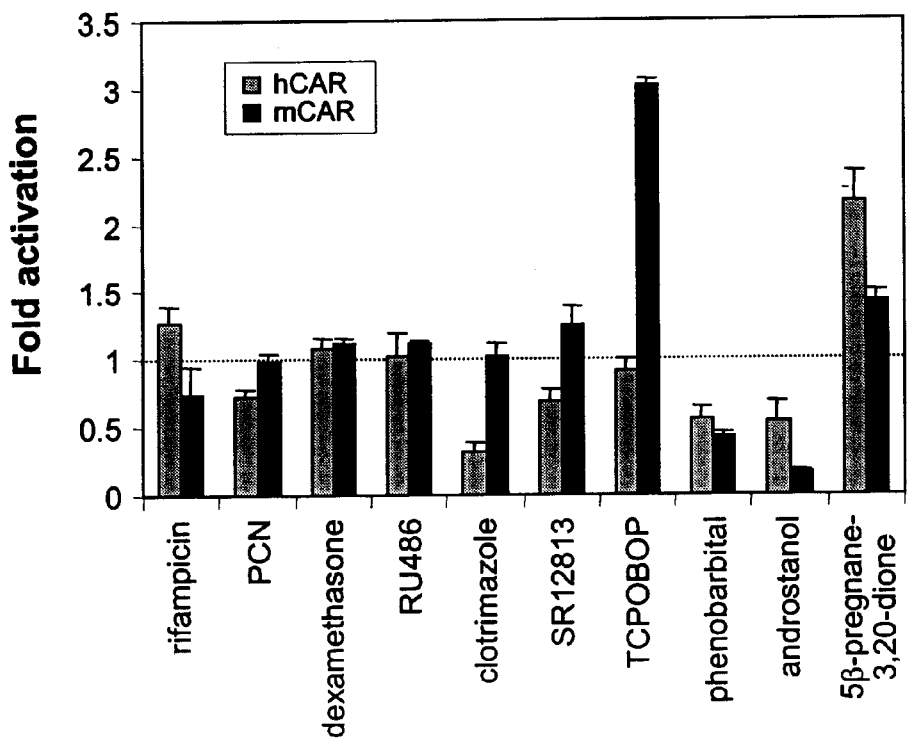
Figure 1C:
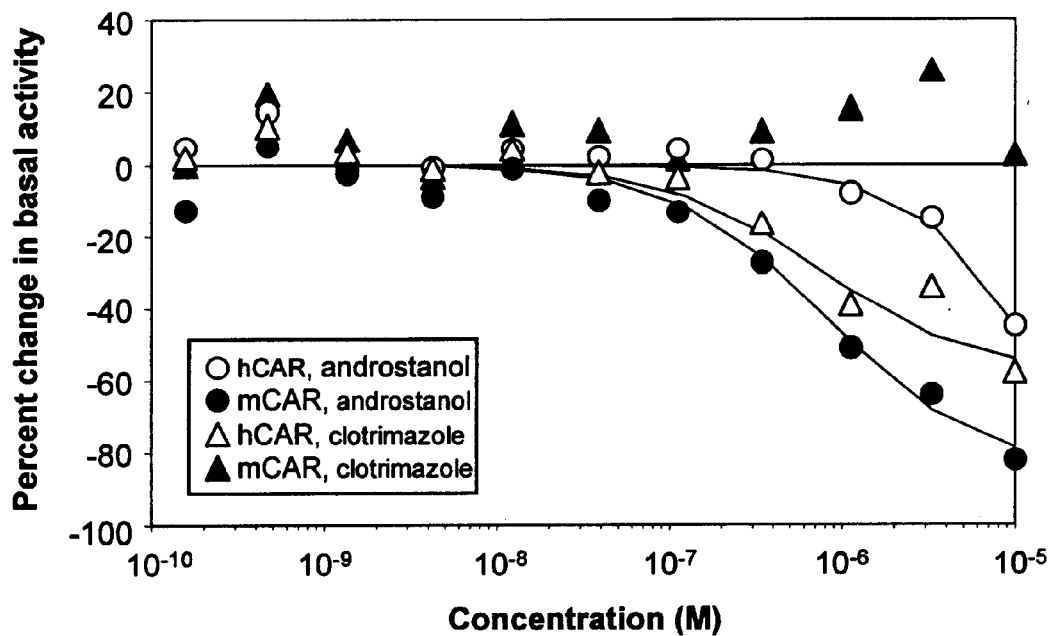

All compounds were initially screened at a concentration of 10 $\mu$M, except for PB which was tested at 0.5 mM. As expected, androstanol was an efficacious deactivator of mCAR (FIG. 1B). Androstanol also deactivated hCAR, though the effect was not nearly as pronounced as on mCAR. By contrast, the antimycotic clotrimazole was an efficacious deactivator of hCAR but not mCAR. Full dose response analysis revealed that clotrimazole deactivated hCAR with an $EC_{50}$ value of ~700 nM (1C and Table 1). Rifampicin, PCN, dexamethasone, RU486, and SR12813 had little or no effect on CAR activity (FIG. 1B). PB caused a weak but reproducible deactivation of both hCAR and mCAR at high concentrations.

Figure 1D:
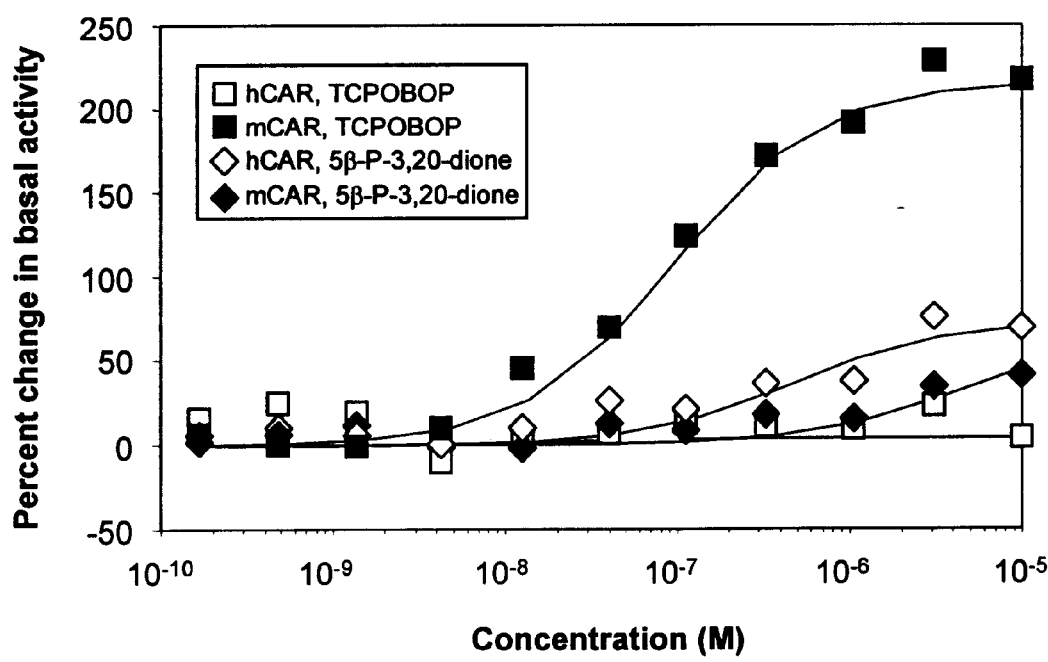
Figure 2A:
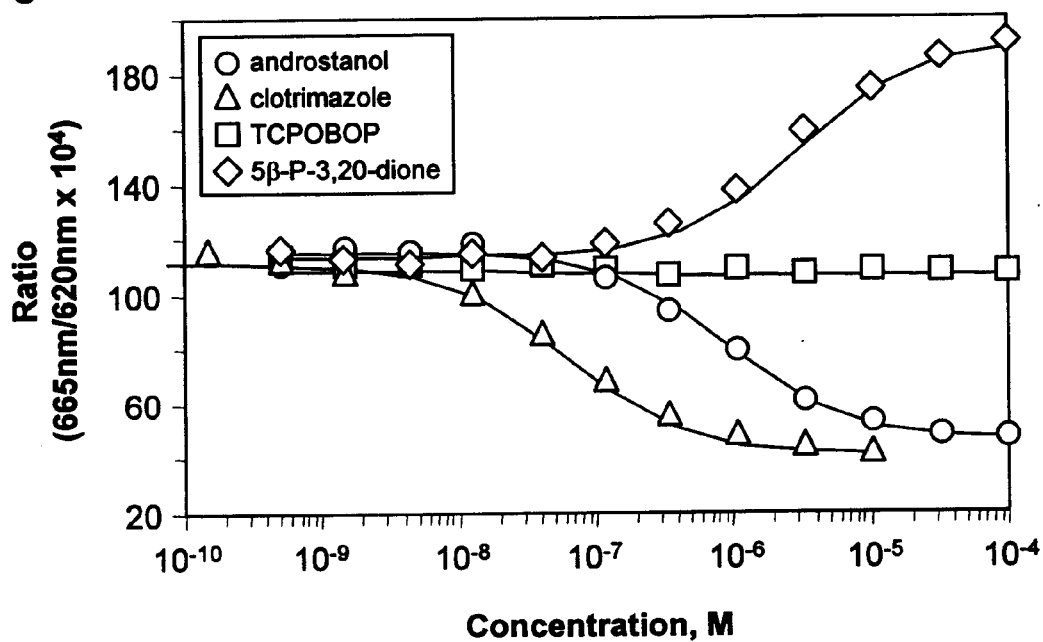
FIGS. 2A and 2B. Compounds induce allosteric changes in hCAR. The FRET ligand sensing assay was run with hCAR (FIG. 2A) or mCAR (FIG. 2B) and the indicated concentrations of 5$\beta$-pregnane-3,20-dione, TCPOBOP, androstanol, and clotrimazole. Data are plotted as (665 nM/620 nM)×10,000.
Figure 2B:
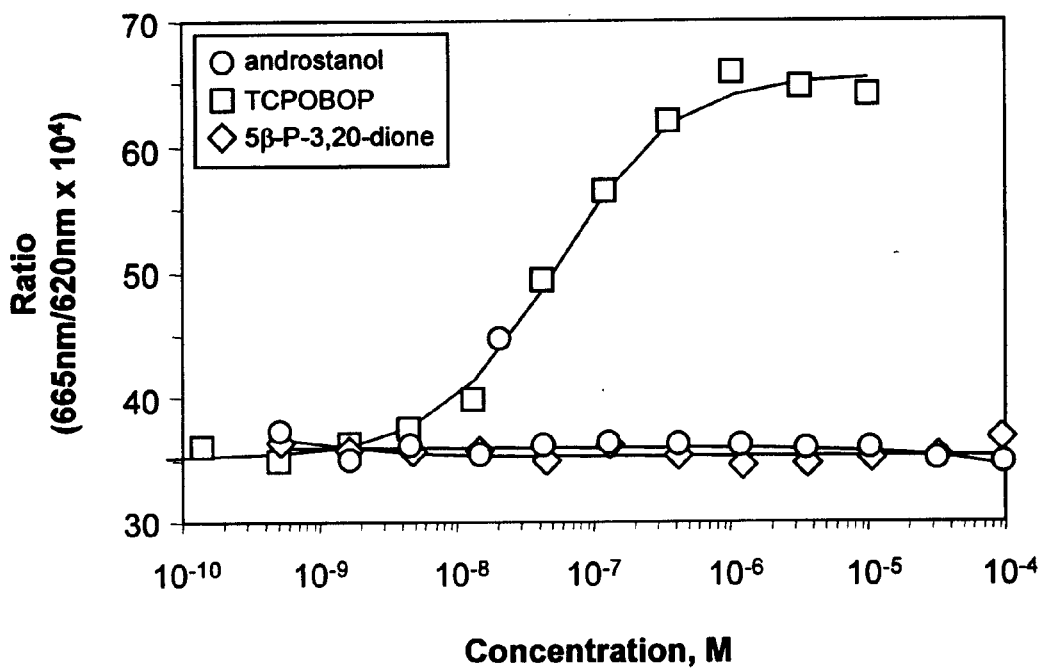

TCPOBOP was a potent ($EC_{50}$~100 nM) and efficacious activator of mCAR but had virtually no activity on hCAR (FIGS. 1B, 2 and Table 1). TCPOBOP was previously shown to activate CAR, albeit weakly, on a reporter construct driven by a PB responsive enhancer module from the CYP2B gene. Interestingly, 5β-pregnane-3,20-dione activated hCAR ~2 fold (FIGS. 1B and 1D) but had only weak effects on mCAR. These data indicate that natural ligands may exist that increase CAR activity above its high constitutive activity.

TABLE 1

$EC_{50}$ values (μM) for activation/deactivation of CAR*

|  | HCAR | mCAR |
|---|---|---|
| rifampicin | — | — |
| PCN | — | — |
| dexamethasone | — | — |
| RU486 | — | — |
| clotrimazole | 0.69 | — |
| SR12813 | — | — |
| TCPOBOP | — | 0.10 |
| androstanol | >10 | 0.84 |
| 5β-pregnane-3,20-dione | 0.67 | — |

*$EC_{50}$ values (μM) are indicated for compounds that either activated or deactivated CAR ≥ 2-fold relative to basal activity (see FIG. 1). Transfected CV-1 cells were treated with concentrations of compound ranging from 0.0001 μM to 10 μM in half-log steps.

Example 2

Compounds Induce Allosteric Changes in the hCAR LBD

Androstanol has previously been shown to inhibit the interaction between CAR and a peptide derived from the steroid receptor coactivator 1 (SRC-1) (Forman et al, Nature 395:612–615 (1998)). It was next tested whether the xenobiotics and steroids that modulated CAR activity in the transfection assay also affected CAR/SRC-1 interactions. A fluorescence resonance energy transfer (FRET) ligand-sensing assay (Parks et al, Science 284:1365–1368 (1999)) was developed for hCAR. The LBD of hCAR was expressed in E. coli, purified to homogeneity, biotinylated, and labeled with the streptavidin-conjugated fluorophore allophycocyanin. Labeled hCAR LBD was incubated with a peptide that included the second LXXLL motif of SRC-1 (amino acids 676 to 700) labeled with europium chelate. As expected, hCAR LBD interacted efficiently with SRC-1 in the absence of compound, and androstanol disrupted this interaction (FIG. 2). Clotrimazole was a potent inhibitor of the hCAR/SRC-1 interaction ($IC_{50}$ ~100 nM) (FIG. 2). Consistent with its ability to activate hCAR in transfection assays, 5β-pregnane-3,20-dione caused a marked increase in the binding of SRC-1 to hCAR (FIG. 2). These results demonstrate that compounds can be identified that induce conformational changes in the hCAR LBD and either enhance or disrupt its basal interaction with SRC-1.

Example 3

Xenobiotics and Steroids Bind hCAR

Figure 3A:
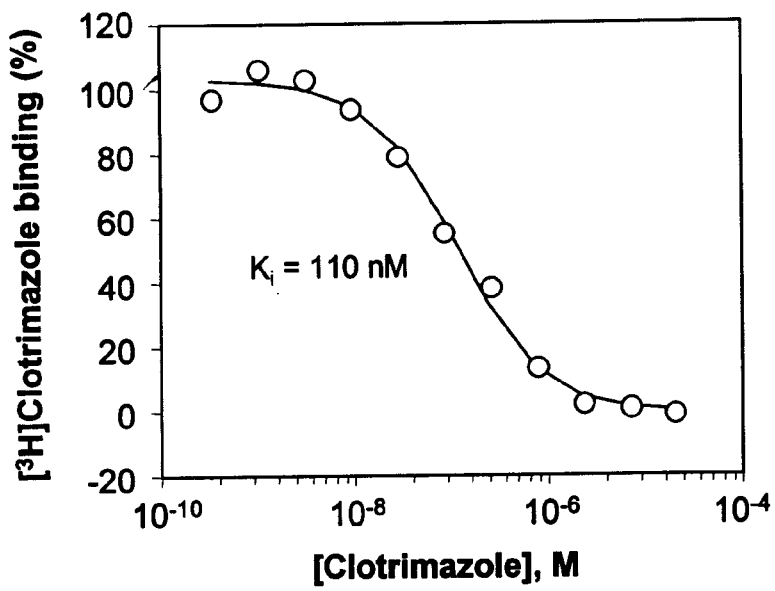
FIGS. 3A and 3B. Clotrimazole and steroids bind hCAR.

The potency of clotrimazole in hCAR cell-based reporter and in vitro FRET assays indicates that [$^3$H]clotrimazole can be used to develop a radioligand binding assay for this orphan receptor. A scintillation proximity binding assay (Nichols et al, Anal. Biochem. 257(2):112–119 (1998)) was developed using the purified biotinylated hCAR LBD and streptavidin-coated polyvinyltoluene SPA beads. [$^3$H] Clotrimazole bound specifically to hCAR with a $K_i$ of ~100 nM (FIG. 3A). These data indicate that clotrimazole mediates its effects on hCAR activity through direct interactions with the receptor LBD.

Figure 3B:
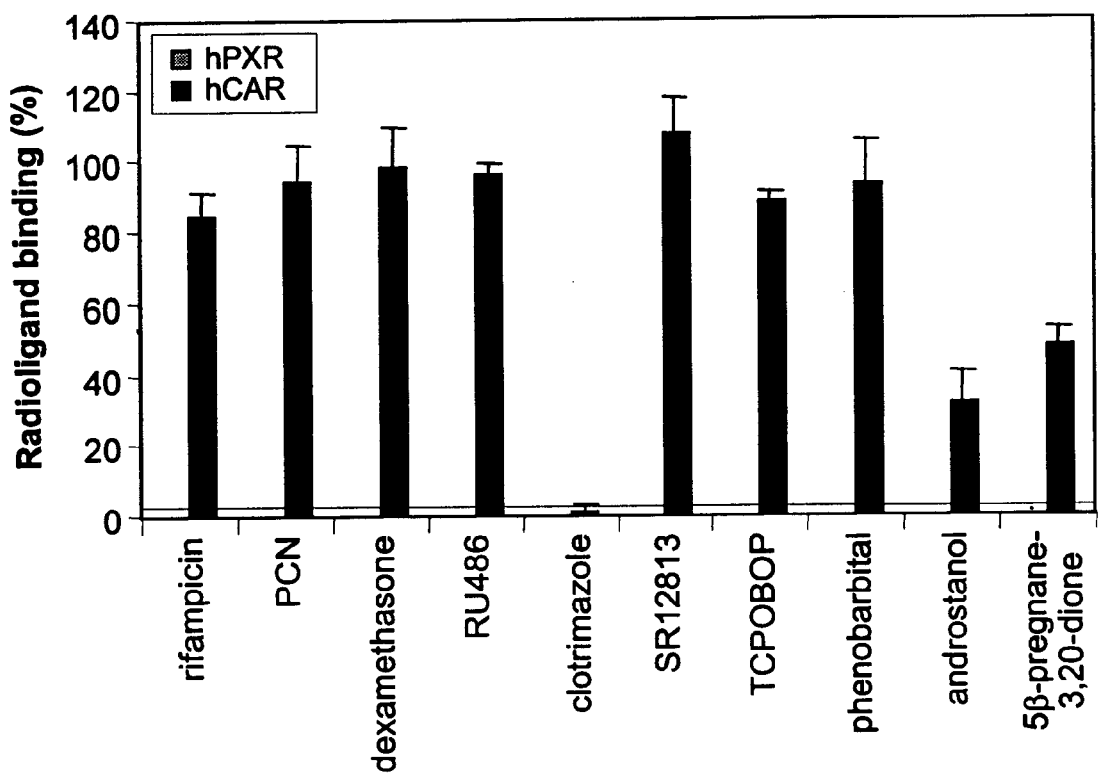

The results of radioligand binding assays for hCAR were in agreement with the transfection data. The sex steroid metabolites androstanol and 5β-pregnane-3,20-dione competed efficiently with [$^3$H]clotrimazole for binding to hCAR. TCPOBOP, dexamethasone RU486, rifampicin, PCN, and SR12813, which had little or no activity on hCAR in the transfection assay, did not compete in the binding assay (FIG. 3B). PB, which deactivated hCAR in the transfection studies, did not compete at a 1 mM concentration with [$^3$H]clotrimazole for binding to hCAR. These data indicate that PB does not mediate its effects on hCAR through direct interactions with the receptor, but rather via an indirect mechanism or through cellular metabolism of PB to a compound that can bind CAR. Many of the structurally-diverse compounds that modulate CAR activity apparently do so through direct interactions with the LBD of this orphan receptor.

All publications referenced in this application are hereby incorporated in their entirety by reference.

Although the present processes have been described with reference to specific details of certain embodiments thereof, it is not intended that such details should be regarded as limitations upon the scope of the invention. One skilled in the art will appreciate from a reading of this disclosure that various changes in form and detail can be made without departing from the true scope of the invention.

What is claimed is:

1. A method of screening a compound for its ability to inhibit the binding of clotrimazole to a Constitutive Androstane Receptor (CAR) ligand binding domain (LBD)-containing polypeptide comprising:
   i) contacting said compound and clotrimazole with said CAR LBD-containing polypeptide under conditions such that clotrimazole can bind to said CAR LBD-containing polypeptide in the absence of said compound, and
   ii) determining the amount of clotrimazole bound to said CAR LBD-containing polypeptide and comparing that amount to an amount of clotrimazole bound to said CAR LBD-containing polypeptide in the absence of said compound, wherein a reduction in the amount of clotrimazole bound to said CAR LBD-containing polypeptide in the presence of said compound indicates that said compound inhibits the binding of clotrimazole to said CAR LBD-containing polypeptide.

2. The method of claim 1 wherein said clotrimazole bears a detectable label.

3. The method of claim 2 wherein said label is a radiolabel.

4. The method of claim 1 wherein said CAR LBD-containing polypeptide is attached to a solid support.

5. The method of claim 4 wherein said solid support is a bead.

6. The method of claim 5 wherein said CAR LBD-containing polypeptide is biotinylated.

7. The method of claim 6 wherein said bead is coated with avidin or streptavidin and said CAR LBD-containing polypeptide is bound to said avidin or streptavidin via said biotin.

8. The method of claim 1 wherein said CAR LBD-containing polypeptide is a CAR LBD fusion protein.

9. The method of claim 1 wherein said CAR LBD-containing polypeptide is CAR LBD.

10. The method of claim 1 wherein said CAR LBD-containing domain comprises human CAR LBD.

11. A method of determining whether a ligand for a selected nuclear receptor other than human Constitutive Androstane Receptor is non-specific for the selected nuclear receptor, comprising
    i) contacting a ligand that binds the selected nuclear receptor with clotrimazole and a human Constitutive Androstane Receptor (hCAR) ligand binding domain (LBD)-containing polypeptide under conditions such that clotrimazole can bind to the hCAR LBD-containing polypeptide in the absence of the ligand, and
    ii) determining the amount of clotrimazole bound to the hCAR LBD-containing polypeptide,
        wherein an amount of clotrimazole bound to the hCAR LBD-containing polypeptide that is less than that bound to the hCAR LBD-containing polypeptide in the absence of ligand indicates that the ligand inhibits binding of clotrimazole to the hCAR LBD-containing polypeptide and is non-specific in its binding to the selected nuclear receptor.

12. A method of screening a compound for ability to bind a human Constitutive Androstane Receptor (hCAR) ligand binding domain (LBD) comprising
    i) contacting the compound and clotrimazole with the hCAR LBD-containing polypeptide under conditions such that clotrimazole can bind the hCAR LBD-containing polypeptide in the absence of the compound, and
    ii) determining the amount of clotrimazole bound to the hCAR LBD-containing polypeptide,
        wherein an amount of clotrimazole bound to the hCAR LBD-containing polypeptide that is less than that bound to the hCAR LBD-containing polypeptide in the absence of the compound indicates that the compound binds the hCAR LBD.

* * * * *

SEQUENCE LISTING

<160> NUMBER OF SEQ ID NOS: 3

<210> SEQ ID NO 1
<211> LENGTH: 257
<212> TYPE: PRT
<213> ORGANISM: homo sapiens
<220> FEATURE:
<221> NAME/KEY: PEPTIDE
<222> LOCATION: (1)...(11)
<223> OTHER INFORMATION: modified histidine tag -continued

```
<400> SEQUENCE: 1

Met Lys Lys Gly His His His His His Gly Pro Val Gln Leu Ser
1               5                   10                  15

Lys Glu Gln Glu Leu Ile Arg Thr Leu Leu Gly Ala His Thr Arg
            20                  25                  30

His Met Gly Thr Met Phe Glu Gln Phe Val Gln Phe Arg Pro Pro Ala
        35                  40                  45

His Leu Phe Ile His His Gln Pro Leu Pro Thr Leu Ala Pro Val Leu
    50                  55                  60

Pro Leu Val Thr His Phe Ala Asp Ile Asn Thr Phe Met Val Leu Gln
65                  70                  75                  80

Val Ile Lys Phe Thr Lys Asp Leu Pro Val Phe Arg Ser Leu Pro Ile
                85                  90                  95

Glu Asp Gln Ile Ser Leu Leu Lys Gly Ala Ala Val Glu Ile Cys His
            100                 105                 110

Ile Val Leu Asn Thr Thr Phe Cys Leu Gln Thr Gln Asn Phe Leu Cys
        115                 120                 125

Gly Pro Leu Arg Tyr Thr Ile Glu Asp Gly Ala Arg Val Gly Phe Gln
130                 135                 140

Val Glu Phe Leu Glu Leu Leu Phe His Phe His Gly Thr Leu Arg Lys
145                 150                 155                 160

Leu Gln Leu Gln Glu Pro Glu Tyr Val Leu Leu Ala Ala Met Ala Leu
                165                 170                 175

Phe Ser Pro Asp Arg Pro Gly Val Thr Gln Arg Asp Glu Ile Asp Gln
            180                 185                 190

Leu Gln Glu Glu Met Ala Leu Thr Leu Gln Ser Tyr Ile Lys Gly Gln
        195                 200                 205

Gln Arg Arg Pro Arg Asp Arg Phe Leu Tyr Ala Lys Leu Leu Gly Leu
210                 215                 220

Leu Ala Glu Leu Arg Ser Ile Asn Glu Ala Tyr Gly Tyr Gln Ile Gln
225                 230                 235                 240

His Ile Gln Gly Leu Ser Ala Met Met Pro Leu Leu Gln Glu Ile Cys
                245                 250                 255

Ser

<210> SEQ ID NO 2
<211> LENGTH: 11
<212> TYPE: PRT
<213> ORGANISM: Artificial Sequence
<220> FEATURE:
<223> OTHER INFORMATION: modified histidine tag

<400> SEQUENCE: 2

Met Lys Lys Gly His His His His His Gly
1               5                   10

<210> SEQ ID NO 3
<211> LENGTH: 5
<212> TYPE: PRT
<213> ORGANISM: homo sapiens
<220> FEATURE:
<221> NAME/KEY: VARIANT
<222> LOCATION: (2)...(3)
<223> OTHER INFORMATION: Xaa = Any amino acid
```

```
<400> SEQUENCE: 3

Leu Xaa Xaa Leu Leu
1               5
```